United States Patent [19]

Burke

[11] Patent Number: 6,015,923

[45] Date of Patent: Jan. 18, 2000

[54] PROCESS FOR THE PREPARATION OF 3-PENTENOIC ACID FROM ALLYLIC BUTENYL ALCOHOLS OR ESTERS USING A NICKEL CATALYST

[75] Inventor: Patrick Michael Burke, Wilmington, Del.

[73] Assignees: E. I. du Pont de Nemours and Company, Wilmington, Del.; DSM N. V., Galeen, Netherlands

[21] Appl. No.: 09/213,186

[22] Filed: Dec. 17, 1998

[51] Int. Cl.$^7$ .................................................... C07C 51/12
[52] U.S. Cl. ............................................................ 562/519
[58] Field of Search .............................................. 562/519

[56] References Cited

U.S. PATENT DOCUMENTS

| | | |
|---|---|---|
| 4,140,865 | 2/1979 | Fernholz et al. ................. 562/519 |
| 4,675,435 | 6/1987 | Hanes et al. . |
| 5,334,755 | 8/1994 | Yoneda et al. ................... 562/519 |
| 5,618,983 | 4/1997 | Burke ................................ 568/454 |

FOREIGN PATENT DOCUMENTS

| | | |
|---|---|---|
| 0 338 730 | 10/1989 | European Pat. Off. . |
| 0 428 979 | 5/1991 | European Pat. Off. . |

*Primary Examiner*—Gary Geist
*Assistant Examiner*—Robert W. Deemie

[57] ABSTRACT

Process for making 3-pentenoic acid acid by reacting an allylic butenyl alcohol or its corresponding ester with carbon monoxide in the presence of nickel, and a source of iodide.

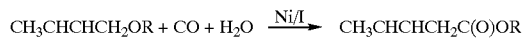

$$CH_3CHCHCH_2OR + CO + H_2O \xrightarrow{Ni/I} CH_3CHCHCH_2C(O)OR$$

6 Claims, No Drawings

PROCESS FOR THE PREPARATION OF 3-PENTENOIC ACID FROM ALLYLIC BUTENYL ALCOHOLS OR ESTERS USING A NICKEL CATALYST

BACKGROUND OF THE INVENTION

3-Pentenoic acid is a well-known intermediate which can be used to make both caprolactam for nylon 6, and adipic acid for nylon 6,6.

EP-A-428979 describes a process for the preparation of 3-pentenoic acid by carbonylation of allylic butenols and butenol esters in the presence of a rhodium catalyst and a promoter selected from hydrogen bromide and hydrogen iodide.

U.S. Pat. No. 4,140,865 describes a process for the manufacture of vinyl acetic acid by reacting allyl alcohol with carbon monoxide in the presence of a cobalt, nickel, rhodium, or palladium catalyst and an iodide source chosen from methyl iodide and palladium iodide.

EP-A-338730 describes the carbonylation of allyl alcohol and allyl acetate in a two-phase system containing a nickel cyanide catalyst and a phase transfer catalyst.

U. S. Pat. No. 5,334,755 describes the carbonylation of methanol in the presence of a Group VIII metal and a pyridine promoter. See U.S. Pat. No. 5,334,755 for example.

BRIEF SUMMARY OF THE INVENTION

The present invention is a process for preparing 3-pentenoic acid by reacting an allylic butenyl alcohol or ester with carbon monoxide in a solvent containing a carboxylic acid in the presence of a source of nickel, a source of iodide, optionally water, and optionally a promoter at a temperature between about 60° C. and about 140° C. and a pressure between about 200 psig and about 4000 psig.

DETAILED DESCRIPTION

In the process of the present invention, an allylic butenyl alcohol or its corresponding ester is reacted with carbon monoxide in the presence of a source of nickel and HI or selected metal iodides in a carboxylic acid-containing solvent. The reaction can be carried out at temperatures in the range of about 60° C. to about 140° C. and pressures in the range of about 200 psig to about 4000 psig. The nickel and iodide combination is believed to act as a catalyst for the reaction. The process may be carried out in the presence of water or hydrogen and/or in the presence of a promoter.

The expression "allylic butenyl alcohol" means cis or trans crotyl alcohol or 3-butene-2-ol.

The allylic butenyl alcohol or ester used in the invention is crotyl alcohol, 3-butene-2-ol or their corresponding carboxylic acid esters.

The nickel portion of the catalyst may be finely divided nickel metal (alone or on a support such as carbon or alumina) or a nickel compound which is or becomes soluble in the reaction medium. Suitable nickel compounds include nickel(II) salts such as nickel acetate or nickel iodide, nickel(O) compounds such as $Ni(COD)_2$ [COD=cyclooctadiene] or $Ni(CO)_2((PC_6H_5)_3)_2$. The nickel catalyst should be used at a concentration between about 20 and about 200 mmoles/liter of reaction medium. The allylic butenyl alcohol or ester conversion rate becomes too slow at lower concentrations of nickel. Higher concentrations of nickel are limited by solubility.

The iodide portion of the catalyst may be HI or any metallic iodide that is capable of generating HI under the reaction conditions. Iodides of the following metals are suitable: B, Al, Ga, Sc, Y, La, Ce, Pr, Nd, Sm, Eu, Gd, Tb, Dy, Ho, Er, Yb, Lu, Ge, Sn, Ti, Zr, Cr, Mo, W, Mn, Fe, Co, Ni and Zn. Highly ionic iodides such as NaI and LiI are not suitable.

The reaction may be promoted further with the use of various promoters. The reaction is strongly promoted by organic nitrogen bases and their iodide salts, for example lutidinium iodide, tetrabutylammonium iodide, methyltriphenylphosphonium iodide. The base strength (pKa) of the base is not critical provided there is an excess of HI over base under the reaction conditions. Bases varying in strength from simple alkylamines and imidazoles to alkyl-substituted ureas and thioureas promote the reaction.

Suitable organic nitrogen bases include pyridine, optionally substituted with $C_1$–$C_5$ alkyl or $C_6$–$C_{20}$ aryl groups. Substituted pyridines such as the isomeric lutidines and even the highly hindered 2,6-di-t-butylpyridine are particularly effective. Polymeric pyridines such as poly(vinylpyridine) may also be used.

Other suitable organic nitrogen bases include quinoline, optionally substituted with alkyl or aryl groups; isoquinoline, optionally substituted with alkyl or aryl groups; imidazole, optionally substituted with alkyl or aryl groups; thiazole, optionally substituted with alkyl or aryl groups; and oxazole, optionally substituted with alkyl or aryl groups. In the above compounds, preferred alkyl substitutents are $C_1$–$C_5$ alkyl groups and preferred aryl substitutents are $C_6$–$C_{20}$ aryl groups, such as phenyl, substituted phenyl, naphthyl, and phenanthryl.

The promoter may also be the hydrogen iodide salt or a quaternary iodide salt of the above organic nitrogen bases. For example, 2,6-lutidinium iodide and 1,3-dimethylimidazolium iodide are effective promoters in the presence of excess hydrogen iodide.

Other suitable organic nitrogen base promoters are alkyl-substituted ureas and thioureas, and aliphatic amides such as N,N-dimethylacetamide.

The promoter may also be an alkyl, aryl or arylalkyl phosphine. The term "aryl" denotes phenyl, substituted phenyls (especially $C_1$–$C_5$ alkyl substituted phenyls), and condensed aromatics such as naphthyl and phenanthryl. The phosphines may be monodentate or bidentate. If a bidentate phosphine is used, it is preferred that it be of the formula $R^3_2P$-$Q$-$PR^4_2$ in which Q is a 3 to 6 carbon atom bridging group and $R^3$ and $R^4$ are the same or different $C_1$–$C_{10}$ alkyl or $C_6$–$C_{20}$ aryl groups. Examples of suitable bidentate phosphines may be found in U.S. Pat. No. 5,618,983, the disclosure of which is incorporated herein by reference.

Molybdenum compounds may also be used as promoters. Compounds of Group VI and Group VII metals (Cr, Mo, W, Mn, Re) may also be used as promoters. Suitable promoters include molybdenum hexacarbonyl, molybdenum(II) acetate dimer, and molybdenum (III) halide, where the halide is chlorine, bromide, or iodide. Preferred is $Mo(CO)_6$, which strongly promotes butadiene carbonylation with Ni/HI, $Ni/AlI_3$ and $Ni/CrI_3$ catalysts.

Preferred reaction conditions are those in which the ratio of iodide to nickel is in the range of 2/1 to 20/1, the ratio of organic nitrogen base or phosphine to nickel is in the range 2/1 to 20/1. The preferred ratio of iodide to promoter depends on the base strength of the promoter. For pyridine bases and for phosphines, this ratio should be greater than one; for weaker organic nitrogen bases such as tetramethylurea, the ratio of iodide to promoter is preferably less than one.

It is preferred to carry out the reaction in the presence of water, which speeds up the reaction and gives a higher yield of 3-pentenoic acid. It is important, however, to limit the amount of water, because too high concentrations can slow the reaction down. Preferred water concentration is in the range of about 1.5% to about 8.0% by weight. The most preferred concentration is about 4.5%.

It is preferred that the reaction is carried out in a solvent that contains a carboxylic acid. When the starting material is an ester (e.g., crotyl acetate) the carboxylic acid solvent is preferred but not necessary. When the starting material is an alcohol, a carboxylic acid solvent is necessary for suitable reactivity. Preferred solvents are carboxylic acids such as acetic acid, propionic acid, glutaric acid or a mixture of these acids. Mixtures of a carboxylic acid and a non-acidic solvent such as toluene, n-butyronitrile or dimethylacetamide may also be used. To facilitate product separation, a carboxylic acid solvent which has a higher boiling point than that of 3-pentenoic acid is preferred.

The reaction of the present invention may be carried out in a batch or continuous type process by heating under Co pressure a mixture of nickel(II) salt, hydrogen iodide, allylic butenyl alcohol or ester, and, preferably, water and a nitrogen base, phosphine or molybdenum carbonyl promoter in a carboxylic acid solvent.

The following are preferred operating conditions:

| Temperature | 90° C.–120° C. |
|---|---|
| CO pressure | 700 to 2000 psig |
| Solvent | Carboxylic Acid |
| Ni concentration | 0.5 to 1.0% by weight |
| Water concentration | 1.5 to 8.0% by weight |
| I/Ni | 5/1 to 10/1 |
| Promoter/Ni | 4/1 to 12/1 |

The invention is illustrated by the following examples, which are not intended to limit the scope of the invention.

EXAMPLES

Example 1

Carbonylation of 3-Acetoxybutene-1 in Acetic Acid at 90° C. and 900 psig with Triphenylphosphine TPP Promoter A 120 mL mechanically stirred Hastelloy-C autoclave was charged with 1.0 g (4 mmole) of nickel acetate, 4.19 g (16 mmole) of triphenylphosphine, 4.49 g 57% aqueous HI (20 mmoles HI+107 mmoles water), 1.7 g (93 mmoles) water and 34 g acetic acid solvent. The solution was heated to a temperature of 90° C. under an initial pressure of 500 psig carbon monoxide. Reaction was initiated by injecting a solution of 11.4 g (100 mmole) of 3-acetoxybutene-1 and 0.5 g 1,2,4-trichlorobenzene (TCB), a gas chromatography (GC) internal standard, and adjusting the total pressure with CO to 900 psig. The total solution volume at room temperature was approximately 50 mL. Carbon monoxide was continuously fed to the autoclave from a reservoir so as to maintain the total pressure constant at 900 psig. Samples were removed at intervals for GC analysis on a 30 M J&W Scientific DBFFAP capillary GC column. The reaction was allowed to run for a total of 3 hours.

The product was a clear yellow homogeneous solution from which some crotyltriphenylphosphonium iodide separated on standing.

The GC analysis of the solutions indicated about 46% of the allylic butenyl acetate (crotyl acetate and its isomer 3-acetoxybutene-1) was consumed in 30 minutes, 59% in 60 minutes, 91% in 180 minutes and 99% in 300 minutes. The major product was 3-pentenoic acid.

Following is a summary of the results of the GC analyses:

| | Moles per mole 3AcB1 Charged | | | | |
|---|---|---|---|---|---|
| Time(Min.) | BD + Butenes | CrX | 3PA | 2M3BA | VL |
| 30 | 1.7 | 53.8 | 23.3 | 0.7 | 0.0 |
| 60 | 5.1 | 40.7 | 41.6 | 1.3 | 0.4 |
| 180 | 1.6 | 8.8 | 74.8 | 2.4 | 2.8 |
| 300 | 2.4 | 1.0 | 84.6 | 2.8 | 7.2 |

BD=butadiene
3AcB1=3-acetoxybutene-1
2M3BA=2-Methyl-3-butenoic acid
CrX=Mixture of Crotyl acetate, 3-Acetoxybutene-1, 3-Iodobutene-1, cis- and trans-crotyl iodides
3PA=cis+trans-3-pentenoic acid
VL=gamma-valerolactone The butenyl acetate and iodide conversion after 6 hours was 99%, the yield of 3-pentenoic acid was 85.5% and the yield of valerolactone was 7.3%. The first order rate constant for the conversion of all C4 precursors (butenyl esters butenyl iodides and butadiene) was 0.72 $Hr^{-1}$, corresponding to a turnover frequency of 13 moles 3AcB1 converted to 3PA per g-atom of Nickel per hour. The space-time yield over the first hour was 730 mmoles 3PA/L/Hr.

Example 2

Carbonylation of 3-Acetoxybutene-1 in Acetic Acid at 100° C. and 900 psi without Promoter The experiment in Example 1 was repeated, except that the phosphine promoter was omitted, the nickel and iodide concentrations were increased by a factor of 2 (16 mmole Ni and 80 mmole HI per 100 mL solution), and the temperature was increased to 100° C. After 3 hours the total conversion of allylic acetates and iodides was 24.7% and the 3PA yield was 71.2%. The first order rate constant was 0.072 $Hr^{-1}$, corresponding to a turnover frequency of 0.65 moles 3AcB1 converted per g-atom of Ni per hour. The space-time yield (STY) was 228 mmole 3PA/L/Hr. The result show that the carbonylation of the allylic acetate to 3PA takes place in good yield in the absence of promoter but the reaction rate is much slower than when a promoter is present.

Example 3

Carbonylation of 3-Acetoxybutene-1 in Anhydrous Acetic Acid at 90° C. and 900 psi with Ni/AlI$_3$/TPP catalyst The experiment in example 1 was repeated, except that the water was omitted, the aqueous HI was replaced with anhydrous aluminum iodide (4 mmoles/100 mL) and the nickel acetate was replaced with anhydrous nickel iodide (4 mmoles/100 mL). The Ni/Iodide/TPP ratio was maintained at 1/5/4).

The butenyl acetate conversion after 6 hours was 41%, the yield of 3-pentenoic acid was 74% and the yield of valerolactone was 1.9%. This sample also showed the presence of significant amounts of acetic anhydride (15.4 moles per mole 3AcB1 charged) and smaller amounts (ca 0.5 Mole %) of the mixed anhydride of 3-pentenoic and acetic acids.

The first order rate constant for the conversion of all C4 precursors (butenyl esters and butadiene) was 0.11 $Hr^{-1}$, corresponding to a turnover frequency of 2.0 moles 3AcB1 converted per g-atom of Nickel per hour.

Example 4

Carbonylation of 3-Acetoxybutene-1 in Acetic Acid at 110° C. and 900 psi with 2,6-Lutidine Promoter The experiment in Example 1 was repeated, except that the temperature was 110° C., the iodide source was NiI$_2$ (2.5 g; 8 mmoles/100 mL), the HI/Ni mole ratio was 8 (Total I/Ni=10), and the promoter was 2,6-lutidine (3.4 g; 32 mmoles). After 5 hours the conversion was 66%, and the yield of 3PA was 93%.

Example 5
Carbonylation of 3-Acetoxybutene-1 using a Nickel catalyst, an Iodide Promoter and Triphenylphosphine Ligand A 25 mL glass-lined pressure vessel was charged with 5 mL of a solution containing 11.4 g (100 mmol) 3-acetoxybutene-1 (3AcB1), 1.00 g (4.0 mmol) of nickel acetate tetrahydrate and 1.00 g 1,2,4-trichlorobenzene (internal GC standard) in 100 mL acetic acid. To the 5 mL aliquot was added 0.225 g of 57% aqueous HI (5 equivalents of HI per equivalent of Ni) and 0.21 g triphenylphosphine (4 equivalents per equivalent of Ni). The pressure vessel was freed from air by purging first with nitrogen (twice) and then with CO (twice). The vessel was then pressurized to 900 psig CO and heated to 90° C. with agitation for 4 hours. The heat was shut off, the pressure vessel was allowed to cool to room temperature and the excess pressure was vented. The product was a clear yellow homogeneous solution. It was analyzed directly by GC on a 30 M J&W Scientific DBFFAP capillary GC column. The results are summarized below:

| Product | mmoles (per 100 mmoles 3AcB1 charged) |
|---|---|
| Butadiene + Butenes | 1.4 |
| 3-Acetoxybutene-1 | 17.5 |
| Crotyl Acetate | 8.1 |
| cis + trans 3-pentenoic acid | 61.1 |
| 2-Methyl-3-butenoic acid | 2.2 |
| Valerolactone | 0.8 |

Conversion of the allylic acetates (3-acetoxybutene-1 and crotyl acetate) to all products was 74%, 3-pentenoic acid yield was 85% and product accounting was 95%.

Small amounts of crotyl pentenoates, vinylcyclohexene, sec-butyl acetate, valeric acid and methylglutaric acid (analyzed as its dimethyl ester after esterification with methanol) were also present.

Example 6
Carbonylation of Crotyl Acetate using a Nickel catalyst and Hydrogen Iodide Promoter The experiment in Example 5 was repeated, except that the 3-acetoxybutene-1 was replaced with an equivalent amount of crotyl acetate (1-acetoxybutene-2). The results are shown in Table 1.

Example 7
Carbonylation of Crotyl Alcohol using a Nickel catalyst and Hydrogen Iodide Promoter The experiment in Example 5 was repeated, except that the 3-acetoxybutene-1 was replaced with an equivalent amount of crotyl alcohol (2-butene-1-ol). The results are shown in Table 1.

Example 8
Carbonylation of 3-Butene-2-ol

The experiment in Example 5 was repeated, except that the 3-acetoxybutene-1 was replaced with an equivalent amount of 3-butene-2-ol. The results are shown in Table 1.

Example 9
Carbonylation of Crotyl Acetate using a Nickel catalyst and Hydrogen Iodide Promoter The experiment in Example 5 was repeated, except that the 3-acetoxybutene-1 was replaced with an equivalent amount of crotyl acetate (1-acetoxybutene-2), the temperature was reduced to 70° C., and the CO pressure was reduced to 500 psig. The results are shown in Table 1.

Example 10
Carbonylation of Crotyl Acetate using a Nickel catalyst and Hydrogen Iodide Promoter The experiment in Example 5 was repeated, except that the 3-acetoxybutene-1 was replaced with an equivalent amount of crotyl acetate (1-acetoxybutene-2), the temperature was reduced to 50° C. and the CO pressure was reduced to 300 psig. The results are shown in Table 1.

TABLE 1

| Ex | Substrate | Temp | Pressure | Conversion | 3PA Yield |
|---|---|---|---|---|---|
| 5 | 3AcB1 | 90 | 900 | 73.8 | 84.7 |
| 6 | CrOAc | 90 | 900 | 67.9 | 89.0 |
| 7 | CrOH | 99 | 900 | 73.1 | 73.3 |
| 8 | 3B2OL | 90 | 900 | 73.3 | 70.8 |
| 9 | CrOAc | 70 | 500 | 42.9 | 74.7 |
| 10 | CrOAc | 50 | 300 | 29.9 | 57.8 |

3AcB1 = 3-Acetoxybutene-1
CrOAc = Crotyl acetate
CrOH = Crotyl alcohol
3B2OL = 3-Butene-2-ol Examples 11–17
Carbonylation of 3-Acetoxybutene-1 using a Nickel catalyst and Various Iodide Promoters The experiment in Example 5 was repeated, except that the hydrogen iodide was replaced with an equivalent iodide amount various metal iodides, and the temperature was varied. The results are shown in Table 2.

TABLE 2

| Ex | Iodide | Temp | Conversion | 3PA Yield |
|---|---|---|---|---|
| 11 | BI$_3$ | 90 | 44 | 63.6 |
| 12 | ZnI$_2$ | 90 | 13 | 20.8 |
| 13 | SnI$_4$ | 90 | 25 | 28.0 |
| 14 | AlI$_3$ | 110 | 85 | 81.7 |
| 15 | CrI$_3$ | 110 | 88 | 86.3 |
| 16 | CoI$_2$ | 110 | 31 | 65.8 |
| 17 | SnI$_4$ | 110 | 35 | 70.1 |

Examples 18–27
Carbonylation of 3-Acetoxybutene-1 using a Nickel catalyst and Various Iodide Promoters The experiment in Example 5 was repeated, except that the triphenylphosphine was replaced with an equivalent amount of various phosphines, and the ratios of HI to Nickel and Phosphorus to Nickel were varied. The results are shown in Table 3.

TABLE 3

| Ex | Ligand | HI/Ni | P/Ni | Conv | 3PA Yield |
|---|---|---|---|---|---|
| 18 | (n-C$_4$H$_9$)$_3$P | 5 | 4 | 61 | 78.5 |
| 19 | C$_2$H$_5$PPh$_2$ | 5 | 4 | 58 | 78.8 |
| 20 | (p-MeOC$_6$H$_4$)$_3$P | 5 | 4 | 54 | 74.3 |
| 21 | (p-ClC$_6$H$_4$)$_3$P | 5 | 4 | 57 | 66.0 |
| 22 | DPPE-O | 5 | 4 | 67 | 75.2 |
| 23 | DPPE-S | 5 | 4 | 61 | 80.6 |
| 24 | (1-Naph)$_3$P | 5 | 4 | 26 | 48.4 |

TABLE 3-continued

| Ex | Ligand | HI/Ni | P/Ni | Conv | 3PA Yield |
|---|---|---|---|---|---|
| 25 | DPPE | 10 | 2 | 25 | 17.9 |
| 26 | DPPP | 10 | 4 | 43.4 | 53.3 |
| 25 | DPPB | 10 | 4 | 84.5 | 82.3 |
| 27 | DPPPent | 10 | 8 | 93.7 | 71.5 |

DPPE-O = Diphenylphosphinoethane monoxide
DPPE-S = Diphenylphosphinoethane monosulfide
DPPE = Diphenylphosphinoethane
DPPP = Diphenylphosphinopropane
DPPB = Diphenylphosphinobutane
DPPPent = Diphenylphosphinopentane
Ph = phenyl
Naph = naphthyl Examples 28–29

Carbonylation of 3-Acetoxybutene-1 using a Heterogeneous Nickel catalyst

The experiment in Example 5 was repeated, except that the nickel acetate was replaced with an equivalent amount of finely divided nickel on Kieselguhr, and the HI/Ni ratio was increased to 10. The results are shown in Table 4.

TABLE 4

| Ex | Nickel Source | Hi/Ni | TPP/Ni | Conv | 3PA Yield |
|---|---|---|---|---|---|
| 28 | Ni/Kiesselguhr | 10 | 4 | 90 | 84.2 |
| 29 | Ni(OAc)$_2$.4H$_2$O | 10 | 4 | 89 | 86.0 |

OAc = acetate

Examples 30–33

Carbonylation of 3-Acetoxybutene-1 using a Nickel catalyst and Isoquinoline

The experiment in Example 4 was repeated, except that the triphenylphosphine was replaced with isoquinoline, the iodide was AlI3 and the ratios of Iodide to Nickel, Isoquinoline to Nickel and water concentration were varied. The results are shown in Table 5.

TABLE 5

| Ex | Temp | Isoq/Ni | I/Ni | H$_2$O/Substrates | Conversion | 3PA Yield |
|---|---|---|---|---|---|---|
| 30 | 120 | 4 | 10 | 2 | 39 | 50.9 |
| 31 | 120 | 4 | 20 | 2 | 51 | 24.9 |
| 32 | 100 | 4 | 20 | 1.5 | 50 | 50.7 |
| 33 | 100 | 8 | 20 | 1.5 | 27 | 21.5 |

Isoq = isoquinoline

Examples 34–38

Carbonylation of 3-Acetoxybutene-1 using a Nickel catalyst and an Iodide Promoter in the absence of water The experiment in Example 4 was repeated, except that the Nickel compound was Ni(CO)$_2$(PPh3)2(Ph=phenyl) (Strem Chemical), the total Ph3P/Ni ratio (including the Ph$_3$P in the Ni complex) was maintained at 4/1, the water was omitted and the iodide was varied. The results are shown in Table 6.

TABLE 6

| Ex | Ni Source | Iodide | I/Ni | Conv | 3PA Yield |
|---|---|---|---|---|---|
| 34 | Ni(CO)$_2$(PPh$_3$)$_2$ | HI (Anh) | 5 | 57 | 71.2 |
| 35 | Ni(CO)$_2$(PPh$_3$)$_2$ | AlI$_3$ | 5 | 34 | 50.3 |
| 36 | Ni(CO)$_2$(PPh$_3$)$_2$ | TiI$_4$ | 5 | 51 | 66.0 |
| 37 | Ni(CO)$_2$(PPh$_3$)$_2$ | CeI$_3$ | 5 | 28 | 57.9 |
| 38 | Ni(CO)$_2$(PPh$_3$)$_2$ | CeI$_3$ | 5 | 37 | 41.5 |

Anh = Anhydrous

Examples 39–42

Carbonylation of 3-Acetoxybutene-1 at High Pressures using a Nickel/HI catalyst and 2,6-Lutidine Promoter The experiment in Example 5 was repeated, except that the temperature was 100° C., nickel compound was NiI$_2$, the Iodide/Ni ratio was 10, the promoter was 2,6-lutidine, the water concentration was 4.5% (2.5/1 H$_2$O/Substrate), and the pressure was varied over the range 1500 to 3000 psig. The results are shown in Table 7.

TABLE 7

| Ex | Pressure (Total) | Conv. | 3PA (mole/100) | 3PA Yield | 2M3BA Yield | VL Yield | Acctg |
|---|---|---|---|---|---|---|---|
| 39 | 1500 | 97.9 | 82.5 | 86.6 | 3.4 | 9.5 | 101 |
| 40 | 2000 | 76.1 | 70.5 | 95.0 | 3.2 | 1.6 | 99 |
| 41 | 2500 | 52.7 | 48.6 | 94.5 | 3.3 | 0.7 | 99 |
| 42 | 3000 | 42.1 | 36.9 | 90.0 | 3.2 | 0.4 | 97 |

Acctg = Product Accounting (100 × X total moles recovered/moles charged)

Examples 43–48

Carbonylation of 3-Acetoxybutene-1 with 2,6-Lutidine Promoter in Different Solvent Systems The experiment in Example 5 was repeated except that the temperature was 100° C., the nickel compound was nickel 2-ethylhexanoate (4 mmole/100 ml), the Iodide/Ni ratio was 10, the promoter was 2,6-lutidine (0.6/1 Promoter/HI mole ratio), the water concentration was 4.5%, and the solvent was varied. The results are shown in Table 8.

TABLE 8

| Ex | Solvent | Conv | mmoles 3PA | Yield |
|---|---|---|---|---|
| 43 | Acetic Acid | 78.1 | 65.6 | 87.5 |
| 44 | Pivalic acid | 55.4 | 31.8 | 59.8 |
| 45 | n-Butyronitrile | 39.7 | 15.2 | 39.8 |
| 46 | Acetonitrile | 46.4 | 21.6 | 48.4 |
| 47 | N-Methylpyrrolidone | 67.7 | 6.9 | 10.6 |
| 48 | Toluene | 17.1 | 1.2 | 2.9 |

Examples 49–65

Carbonylation of 3-Acetoxybutene-1 using a Nickel catalyst and Various Nitrogen Base Promoters The experiment in Example 5 was repeated, except that the temperature was 110° C., the nickel acetate concentration was 8 mmoles/100 mL, the HI/Ni ratio was 10, the promoter/Ni ratio was 4, the water concentration was 7.7%. and the promoter was varied. The results are shown in Table 9.

TABLE 9

| Ex | Promoter | Conv | Yield 3PA | Yield 2M3BA | Yield VL |
|---|---|---|---|---|---|
| 49 | None (10HI/Ni) | 39.9 | 15.3 | 0.0 | 0.0 |
| 50 | Pyridine | 82.5 | 64.1 | 3.1 | 4.1 |
| 51 | 2,6-Di-t-Butyl-Pyridine | 77.9 | 70.4 | 3.9 | 7.9 |
| 52 | 2,6-Diphenylpyridine | 92.3 | 59.6 | 3.5 | 12.8 |
| 53 | 3,4-Lutidine | 80.9 | 61.6 | 3.4 | 4.6 |
| 54 | 4-Picoline | 79.6 | 62.2 | 3.3 | 4.1 |
| 55 | 2-Ethylpyridine | 77.4 | 62.1 | 3.2 | 3.7 |
| 56 | 3-Benzoylpyridine | 75.3 | 41.5 | 2.3 | 3.2 |
| 57 | Isoquinoline | 83.2 | 57.2 | 3.3 | 4.7 |
| 58 | Tributylamine | 78.7 | 61.3 | 3.4 | 3.1 |
| 59 | N,N,N',N'-Tetramethylethylenediamine | 54.6 | 48.4 | 3.1 | 0.0 |
| 60 | Triphenylamine | 70.2 | 57.5 | 2.9 | 2.3 |
| 61 | Diphenylethylamine | 84.5 | 63.1 | 3.3 | 10.4 |
| 62 | N,N-Di Methylaniline | 62.5 | 11.2 | 0.0 | 0.0 |
| 63 | 4-methylimidazole | 90.0 | 61.4 | 3.3 | 10.4 |
| 64 | N,N'-Dibutylthiourea | 57.5 | 57.4 | 3.2 | 6.0 |
| 65 | Polyvinylpyridine (2% cross-linked, 8 eq/Ni) | 46.6 | 61.8 | 4.2 | — |

Examples 66–76

Carbonylation of 3-Acetoxybutene-1 using a Nickel catalyst and Various Iodide Salt Promoters The experiment in Example 5 was repeated, except that the temperature was 115° C., the nickel acetate concentration was 4 mmoles/100 mL, the HI/Ni ratio and the promoter/Ni ratio were varied, the water concentration was 4.5%, and the promoter was varied. The results are shown in Table 10.

TABLE 10

| Ex | Promoter | Prom/Ni | HI/Ni | Conv | Yield 3PA |
|---|---|---|---|---|---|
| 66 | None (4HI/Ni) | 0 | 4 | 29.2 | 53.7 |
| 67 | None (4HI/Ni) | 0 | 10 | 36.8 | 62.8 |
| 68 | 1,3-Dimethylimidazolium iodide | 6 | 4 | 45.1 | 66.3 |
| 69 | 1,3-Dimethylimidazolium iodide | 6 | 10 | 76.6 | 81.9 |
| 70 | Ethylquinaldinium Iodide | 6 | 4 | 43.6 | 71.9 |
| 71 | 1,4-dimethylpyridinium iodide | 6 | 4 | 47.3 | 76.3 |
| 72 | Methyltriphenylphosphonium iodide* | 4 | 5 | 33.5 | 68.3 |
| 73 | 3-Ethyl-2-methyl-2-thiazolium iodide | 6 | 4 | 43.6 | 58.8 |
| 74 | Tetrabutylammonium iodide | 6 | 4 | 80.1 | 87.9 |
| 75 | Tetrabutylammonium iodide | 10 | 5 | 81.5 | 85.6 |
| 76 | 2,6-Lutidinium iodide | 6 | 4 | 73.9 | 88.4 |

*Run at 100 C.

Examples 77–83

Carbonylation of 3-Acetoxybutene-1 using a Nickel catalyst and an Mo, W or Re Promoter.

The experiment in Example 5 was repeated, except that the temperature was 100° C., nickel acetate concentration was 8 mmoles/100 mL, the iodide and promoter were varied, the I/Ni ratio was 5, the promoter/Ni ratio and water concentration were varied, The results are shown in Table 11.

TABLE 11

| Ex | % $H_2O$ | Iodide | Promoter | Metal/Ni | Conv | Yield 3PA |
|---|---|---|---|---|---|---|
| 77 | 1.8 | $AlI_3$ | $Mo(CO)_6$ | 4 | 94.5 | 73.1 |
| 78 | 1.8 | $AlI_3$ | $Mo(CO)_6$ | 12 | 94.2 | 90.4 |
| 79 | 3.9 | HI | None | 0 | 40.2 | 47.4 |
| 80 | 3.9 | HI | $Mo(CO)_6$ | 8 | 79.9 | 76.7 |
| 81 | 3.9 | HI | $[Mo(OAc)_2]_2$ | 8 | 62.2 | 69.5 |
| 82 | 3.9 | HI | $W(CO)_6$ | 8 | 34.3 | 60.7 |
| 83 | 3.9 | HI | $Re_2(CO)_{10}$ | 8 | 38.4 | 58.3 |

What is claimed is:

1. A process for making 3-pentenoic acid which comprises (1) reacting an allylic butenyl alcohol or allylic butenyl ester with carbon monoxide in the presence of nickel and an iodide source selected from the group consisting of HI and iodides of metals selected from the group consisting of B, Al, Ga, Sc, Y, La, Ce, Pr, Nd, Sm, Eu, Gd, Tb, Dy, Ho, Er, Yb, Lu, Ge, Sn, Ti, Zr, Cr, Mo, W, Mn, Fe, Co, Ni and Zn at a temperature between about 60° C. and about 140° C. and a pressure between about 200 psig and about 4000 psig in a carboxylic acid solvent, and (2) recovering 3-pentenoic acid.

2. The process of claim 2 in which the reaction is carried out in the presence of water.

3. The process of claim 2 in which the butadiene and carbon monoxide are reacted in the presence of a promoter selected from the group consisting of trialkylamine, wherein each alkyl contains from 1 to 5 carbon atoms, or a hydrogen iodide or quarternary ammonium iodide salt thereof;

arylalkylamine, wherein each aryl group contains from 6 to 20 carbon atoms and each alkyl contains from 1 to 5 carbon atoms, or a hydrogen iodide or quarternary ammonium iodide salt thereof;

triarylamine, wherein each aryl group contains from 6 to 20 carbon atoms, or a hydrogen iodide or quarternary ammonium iodide salt thereof;

pyridine, optionally $C_1$–$C_5$ alkyl- or $C_6$–$C_{20}$ aryl-substituted, or a hydrogen iodide or quarternary ammonium iodide salt thereof;

quinoline, optionally $C_1$–$C_5$ alkyl- or $C_6$–$C_{20}$ aryl-substituted, or a hydrogen iodide or quarternary ammonium iodide salt thereof;

isoquinoline, optionally $C_1$–$C_5$ alkyl- or $C_6$–$C_{20}$ aryl-substituted, or a hydrogen iodide or quarternary ammonium iodide salt thereof;

imidazole, optionally $C_1$–$C_5$ alkyl- or $C_6$–$C_{20}$ aryl-substituted, or a hydrogen iodide or quarternary ammonium iodide salt thereof;

thiazole, optionally $C_1$–$C_5$ alkyl- or $C_6$–$C_{20}$ aryl-substituted, or a hydrogen iodide or quarternary ammonium iodide salt thereof;

oxazole, optionally $C_1$–$C_5$ alkyl- or $C_6$–$C_{20}$ aryl-substituted, or a hydrogen iodide or quarternary ammonium iodide salt thereof;

$C_1$–$C_5$ alkyl-substituted urea or thiourea; aliphatic amide;

trialkylphosphine, wherein each alkyl contains from 1 to 5 carbon atoms;

triarylphosphine, wherein each aryl group contains from 6 to 20 carbon atoms;

dialkylarylphosphine, wherein the aryl group contains from 6 to 20 carbon atoms and each alkyl contains from 1 to 5 carbon atoms;

alkyldiarylphosphine, wherein each aryl group contains from 6 to 20 carbon atoms and the alkyl contains from 1 to 5 carbon atoms;

bidentate phosphine of the formula $R^3_2P$-Q-$PR^4_2$ in which Q is a 3 to 6 carbon atom bridging group and $R^3$ and $R^4$ are the same or different $C_1$–$C_{10}$ alkyl or $C_6$–$C_{20}$ aryl groups; and compounds of Group VI and VII metals of the Periodic Table.

4. The process of claim 3 in which, the iodide source is HI, the temperature is in the range of 100° C. to 120° C., the CO pressure is in the range of 900 psig to 1800 psig, and the solvent is a monocarboxylic acid or a dicarboxylic acid containing 1 to 10 carbon atoms.

5. The process of claim 4 in which the nickel is in the form of a Ni(II) salt.

6. The process of claim 5 where the promoter is selected from the group consisting of molybdenum hexacarbonyl, molybdenum(II) acetate dimer, and molybdenum (III) halide, where the halide is chlorine, bromide, or iodide.

* * * * *